United States Patent
Qiu et al.

(10) Patent No.: US 10,201,275 B1
(45) Date of Patent: Feb. 12, 2019

(54) REFLECTIVE ULTRA-WIDE FIELD FUNDUS IMAGER

(71) Applicant: Carl Zeiss Meditec, Inc., Dublin, CA (US)

(72) Inventors: Yue Qiu, Pleasanton, CA (US); Matthew Everett, Livermore, CA (US); Jochen Straub, Pleasanton, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 25 days.

(21) Appl. No.: 15/415,116

(22) Filed: Jan. 25, 2017

Related U.S. Application Data (60) Provisional application No. 62/293,068, filed on Feb. 9, 2016.

(51) Int. Cl.
| | |
|---|---|
| *A61B 3/12* | (2006.01) |
| *A61B 3/10* | (2006.01) |
| *G02B 26/10* | (2006.01) |

(52) U.S. Cl.
CPC .............. *A61B 3/12* (2013.01); *A61B 3/1025* (2013.01); *G02B 26/105* (2013.01)

(58) Field of Classification Search
CPC ......... A61B 3/13; A61B 3/1025; A61B 3/102; A61B 3/12; A61B 3/14; A61B 2017/00694; A61B 3/1225; A61B 5/0073; A61B 3/0091; A61B 3/10; A61B 3/1015; A61B 3/1241; A61B 5/0059; A61B 2017/22087; A61B 3/0016

See application file for complete search history.

(56) References Cited

U.S. PATENT DOCUMENTS

| | | |
|---|---|---|
| 5,815,242 A | 9/1998 | Anderson et al. |
| 6,288,784 B1 | 9/2001 | Hitzenberger et al. |
| 7,959,290 B2 | 6/2011 | Cairns et al. |
| 9,078,603 B2 | 7/2015 | Thomson et al. |
| 2010/0141895 A1 | 6/2010 | Cairns et al. |
| 2010/0150415 A1 | 6/2010 | Atkinson et al. |
| 2012/0133888 A1 | 5/2012 | Gray et al. |
| 2013/0093996 A1 | 4/2013 | Thomson et al. |
| 2013/0128224 A1 | 5/2013 | Wall et al. |
| 2013/0128225 A1 | 5/2013 | Wall et al. |
| 2013/0135583 A1 | 5/2013 | Gray et al. |
| 2013/0335703 A1 | 12/2013 | Creasey et al. |
| 2014/0327882 A1 | 11/2014 | Muyo et al. |
| 2015/0216408 A1 | 8/2015 | Brown et al. |
| 2015/0282707 A1 | 10/2015 | Tanabe et al. |

*Primary Examiner* — Jack Dinh
(74) *Attorney, Agent, or Firm* — Morrison & Foerster LLP (57) ABSTRACT

Improved scanning ophthalmoscopes for scanning the retina of an eye are discussed in the present disclosure. One example scanning ophthalmoscope includes an uncollimated light source, a first scanning element, a second scanning element, a slit of a first aspherical mirror, and a second aspherical mirror. The uncollimated light source produces a beam of light to illuminate the retina. The beam of light is relayed from the first scanning element onto the second scanning element by the slit of the first aspherical mirror. The second aspherical mirror relays the beam of light from the second scanning element to the pupil of the eye.

5 Claims, 12 Drawing Sheets

REFLECTIVE ULTRA-WIDE FIELD FUNDUS IMAGER

PRIORITY

The present application claims priority to U.S. Provisional Application Ser. No. 62/293,068 filed Feb. 9, 2016, the contents of which are hereby incorporated by reference.

BACKGROUND

The present invention relates to improved scanning ophthalmoscopes for scanning the retina of an eye.

Some of the previous scanning ophthalmoscopes are described by U.S. Pat. Nos. 5,815,242 and 7,959,290, and US Publication No. 2013/0093996, each of which is hereby incorporated by reference. In particular, U.S. Pat. No. 5,815,242 describes a scanning laser ophthalmoscope which produces images of the rear surface of the human eye, and particularly of the retina, by utilizing an aspherical mirror to reflect light beams, produced by multiple scanning laser light sources, into the retina. The scanning laser ophthalmoscope comprises a laser light source, a first scanning system, a second scanning system, and an aspherical mirror. The laser light source, the first scanning system, and the second scanning system are adapted to combine to provide a two-dimensional laser light scan from an apparent point source. The aspherical mirror has two foci and is adapted to transfer the two-dimensional laser light scan from the apparent point source into the eye. The scanning laser ophthalmoscope is adapted to provide the apparent point source at a first focus of the aspherical mirror and to accommodate the eye at a second focus of the mirror.

U.S. Pat. No. 7,959,290 describes a scanning ophthalmoscope for scanning the retina of an eye comprising a source of collimated light, a first scanning element, a second scanning element, a scan compensation device, and a scan transfer device. The first scanning element produces a one-dimensional collimated light scan in a first direction. The scan compensation device delivers the one-dimensional collimated light scan from the first scanning element onto the second scanning element in a manner that the scan in the first direction appears to be provided from an apparent point source. The second scanning element produces from the one-dimensional collimated light scan a two-dimensional collimated light scan by scanning in a second direction from the apparent point source. The scan transfer device transfers the two-dimensional collimated light scan from the apparent point source into the eye.

US Publication No. 2013/0093996 describes a scanning ophthalmoscope for scanning the retina of an eye and a method of scanning the retina of an eye. The ophthalmoscope comprises a source of collimated light, a first scanning element, a second scanning element, a scan relay device, and a scan transfer device. The source of collimated light, the first and second scanning elements, and the scan relay device combine to provide a two-dimensional collimated light scan from an apparent point source. The scan transfer device transfers the two-dimensional collimated light scan from the apparent point source into the eye.

Here we describe further improved scanning ophthalmoscopes and/or apparatuses, which are capable of not only performing point scanning of the retina but also, in some embodiments, the line scanning of the retina.

SUMMARY

According to one aspect of the subject matter described in the present application, a scanning ophthalmoscope for scanning the retina of an eye comprises an uncollimated light source for producing a beam of light to illuminate the retina; a first scanning element; a second scanning element; a slit of a first aspherical mirror, wherein the beam of light from the first scanning element is relayed onto the second scanning element by the slit of the first aspherical mirror; and a second aspherical mirror for relaying the beam of light from the second scanning element to the pupil of the eye.

According to another aspect of the subject matter described in the present application, a scanning ophthalmoscope for scanning the retina of an eye comprises a light source for producing a beam of light to illuminate a line on the retina; a pupil splitting element for separating light illuminating the retina and light returning from the retina; a scanning element; a slit of a first aspherical mirror for relaying light from the pupil splitting element onto the scanning element to provide a scanning line; and a second aspherical mirror for transferring the scanning line from the scanning element into the pupil of the eye.

According to yet another aspect of the subject matter described in the present application, a scanning ophthalmoscope for scanning the retina of an eye through the pupil comprises a light source for illuminating the retina with one or more rays of light; at least one aspherical mirror having astigmatism; a first scanning element; and a second scanning element, wherein the first scanning element and the second scanning element are placed in a way such that (a) a ray of light when incident on the first scanning element travels to the second scanning element without being reflected by the aspherical mirror, and (b) the pupil is imaged to the first scanning element for rays travelling in a first plane defined by the direction of astigmatism and optical axis, and the pupil is imaged to the second scanning element for light rays travelling in the plane perpendicular to the first plane.

It should be noted that the various scanning ophthalmoscopes discussed in the present disclosure are not limited to use with elliptical mirrors and slits of the elliptical mirrors, and that aspherical mirrors and slits of the aspherical mirrors are also possible for use with these ophthalmoscopes and are within the scope of the present invention.

It should further be noted that the terms "slit elliptical mirror" and "elliptical mirror" are used throughout this disclosure to refer to two different sizes of an elliptical mirror. An elliptical mirror is a portion of an elliptical surface with a normal elliptical, circular, or rectangular clear aperture. The term "slit elliptical mirror" or "slit of an elliptical mirror" refers to a part/portion of the elliptical mirror with a relatively large width to height ratio (e.g., 5:1 or 10:1) that can be used for relaying light from one element to another. These terminologies are further clearly demonstrated in FIGS. 3A and 3B, where reference numeral 302 represents an elliptical mirror 302 and reference numerals 104a or 104b represents a slit of the elliptical mirror 302.

Furthermore, it should be understood that the language used in the specification has been principally selected for readability and instructional purposes and not to limit the scope of the inventive subject matter.

DETAILED DESCRIPTION

All patent and non-patent references cited within this specification are herein incorporated by reference in their entirety to the same extent as if the disclosure of each individual patent and non-patient reference was specifically and individually indicated to be incorporated by reference in its entirely.

Various point and line scanning ophthalmoscopes are now discussed in detail below with references to the figures. It should be noted that even though all these ophthalmoscopes are discussed and shown for use with an elliptical mirror and/or slit of an elliptical mirror, since an elliptical mirror is just one type of aspheric mirror, each of these ophthalmoscopes can be generalized to function with an aspheric mirror and/or a slit of an aspheric mirror as well.

Point Scanning Ophthalmoscope

Figure 1A:
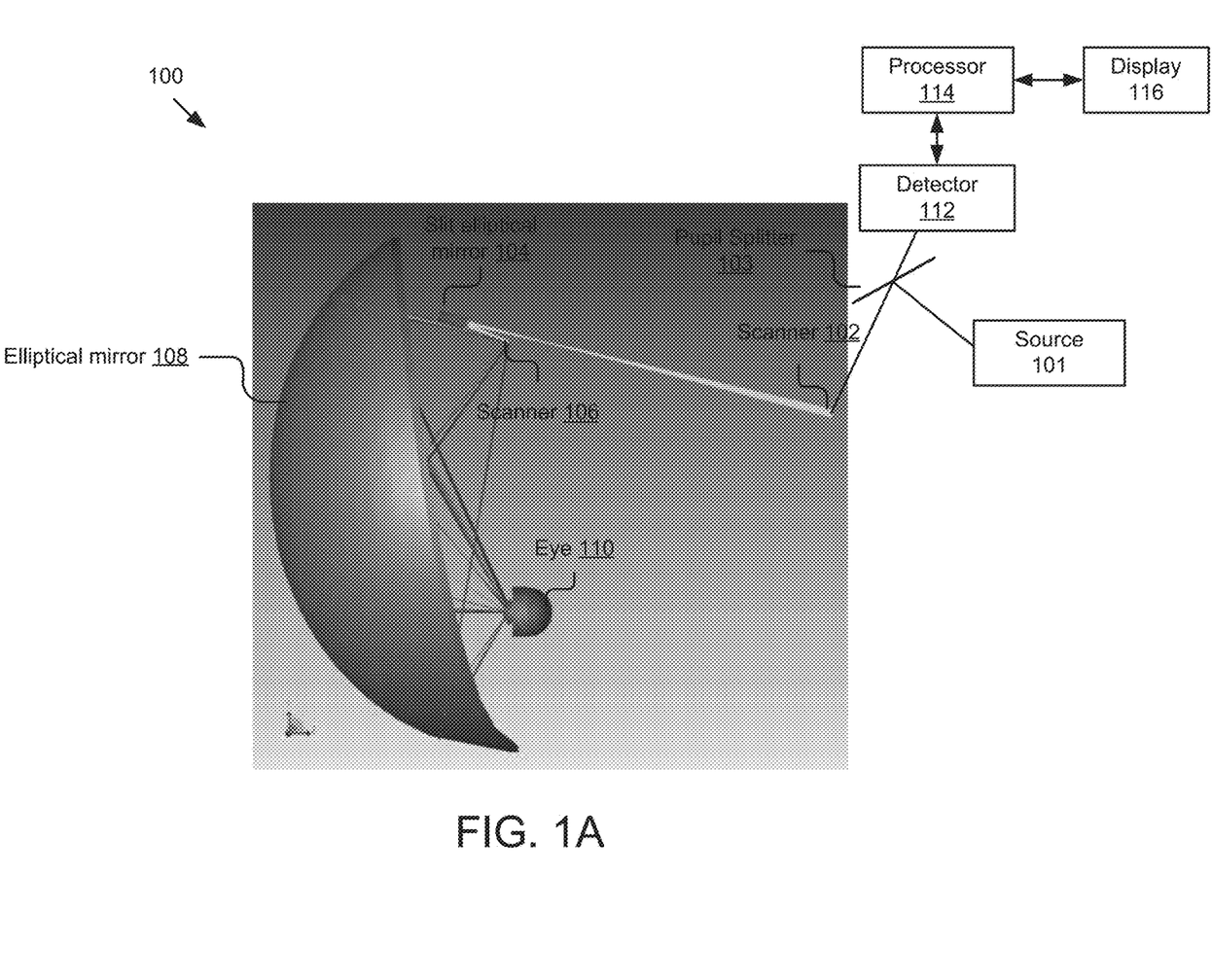
FIG. 1A illustrates a side view of a point scanning ophthalmoscope that is capable of performing a point scan of the retina of an eye.

FIG. 1A illustrates a side view of a general point scan ophthalmoscope 100 that is capable of performing a point scan of the retina of an eye. Point scanning of the retina means scanning the retina point by point over two dimensions and the image of the retina is reconstructed based on the scanned points. As depicted, the scanning ophthalmoscope system 100 comprises a source of light 101, a first scanner or scanning element 102, a pupil splitter 103, a slit 104 of an elliptical mirror (referred to herein as a slit elliptical mirror 104), a second scanner or scanning element 106, an elliptical mirror 108, a detector 112, a processor 114, and a display 116. As mentioned earlier, the slit 104 could be generalized to be a slit of an aspherical mirror and the elliptical mirror 108 could be an aspherical mirror.

Figure 2A:
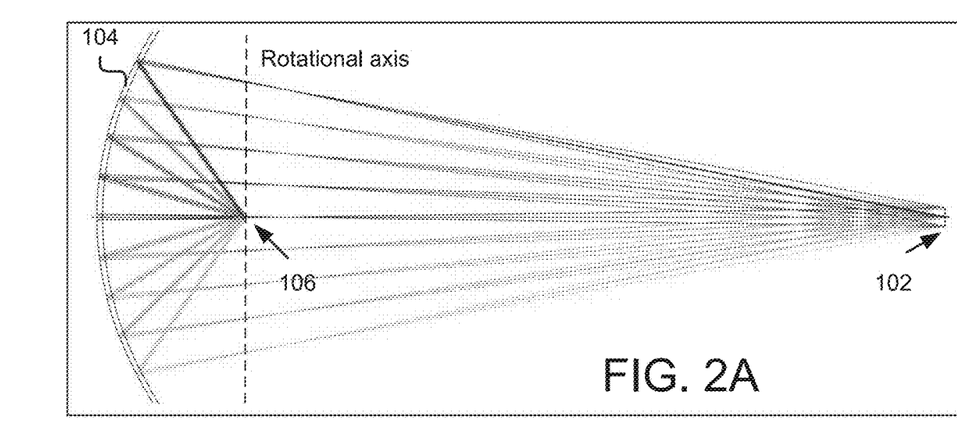
FIGS. 2A and 2B illustrate a top view and a side view of a slit of an elliptical mirror (shown in FIGS. 1A-1C) and scanners arranged at its two focus points, respectively.
Figure 2B:
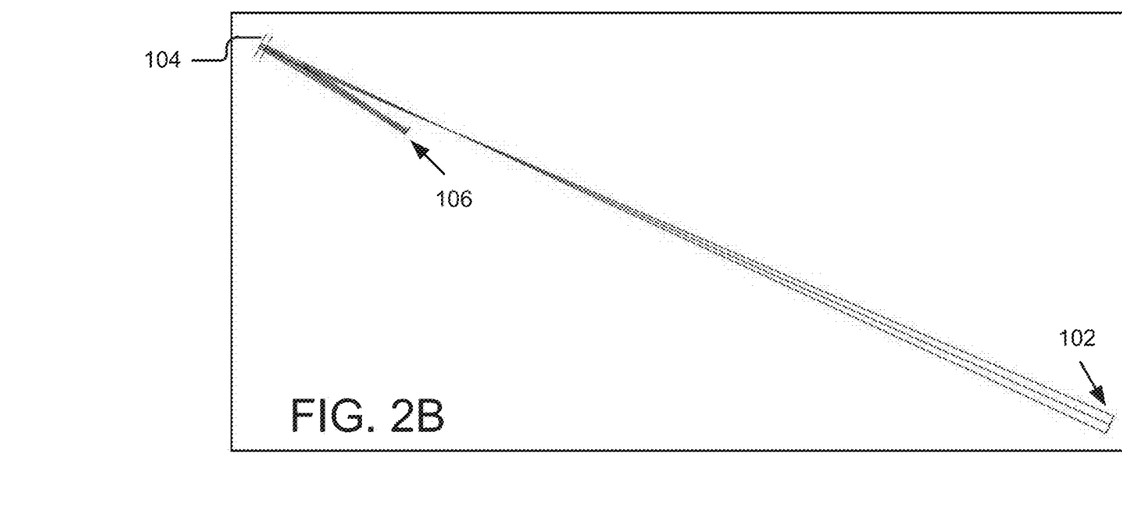

The source of light 101 used in the scanning ophthalmoscope can be either a collimated light source or an uncollimated light source. It is advantageous to use an uncollimated light source for obtaining sharp retinal images. For a given eye, the degree of convergence or divergence of the light beam needs to vary depending on the point of the retina that is scanned. By using the uncollimated light source, the range of convergence or divergence is adjustable for eyes with different refractive error. In some embodiments, the source of light 101 used in the scanning ophthalmoscope may be a laser producing a laser beam, which is incident on the first scanning element 102 via the pupil splitter 103. The pupil splitter or splitting element 103 may be any element that separates light illuminating the retina from light that is returning from the retina. For example, the pupil splitting element can be an optical element with two parts, where one part is reflective for illumination purposes and the other part is transmissive for observation purposes. The first scanning element 102 can be a high speed rotating polygon mirror and the second scanning element 106 can be a slow speed oscillating plane mirror or vice versa. The slit elliptical mirror 104 has two foci and the two scanning elements 102 and 106 are located at the two foci of the mirror 104. For instance, the first scanning element 102 is located at the first focus of the mirror 104 and the second scanning element 106 is located at the second focus of the mirror 104, as shown for example in FIGS. 2A, 2B, and 3A. In some embodiments, the positioning of the two scanning elements 102 and 106 at the two focus points of the mirror 104 depends on whether the mirror is on-axis or off-axis. For instance, if the mirror is off-axis, then the two scanning elements 102 and 106 are located at the two focus points of the mirror (for example, see FIG. 3A). Whereas, if the mirror is on-axis, then the two scanning elements 102 and 106 are located off the two focus points of the mirror (for example, see FIG. 3B). This is further discussed below with respect to FIGS. 3A and 3B.

The first scanning element 102 and the second scanning element 106 are each capable of generating one dimensional light scan(s) of the laser beam in a particular direction (e.g., vertical, horizontal, etc.). The first scanning element 102 and the second scanning element 106 thus together create a two-dimensional light scan in the form of a raster scan pattern. For instance, the first scanning element 102 produces a one-dimensional light scan in a first direction (e.g., vertical) when a light beam from the light source (not shown) is incident on the first scanning element 102. The one-dimensional light scan then travels to the second scanning element 106 by the slit elliptical mirror 104 where they are combined with a one-dimensional light scan produced by the second scanning element 106 in a second direction (e.g., horizontal) to create the two dimensional light scan.

The elliptical mirror 108 also has two foci. The second scanning element 106 is located at the first focus of the mirror 108 and a subject's eye 110 is located at the second focus of the mirror 108. The elliptical mirror 108 and the second scanning element 106 are arranged such that the rotational axis of the second scanning element 106 is substantially perpendicular to the line joining the two foci of the elliptical mirror 108. The elliptical mirror 108 projects the two dimensional scan provided by the second scanning element 106 onto the subject's eye 110 for scanning the retina. A beam reflected from the retina of the subject's eye 110 is conveyed back through the scanning ophthalmoscope and directed onto the detector 112 via pupil splitter 103. The collected light is sent to the processor 114, which is used to produce an image of the subject's retina. The resulting image can be displayed on the display 116 or stored in memory for future reference and processing.

The slit elliptical mirror 104 described herein serves two important functions. A first function of the mirror 104 is that of a scan transfer of the laser beam from the first scanning element 102 to the second scanning element 106. This function of the slit elliptical mirror 104 is more clearly illustrated in FIGS. 2A and 2B that show a top view and a side view arrangement of the mirror 104 relative to the two scanning elements 102 and 106, respectively. The mirror 104 provides point to point transfer, without introducing any translational component, which would cause failure of the laser beam to enter through the pupil of the subject's eye 110. Thus, the laser beam appears to come from an apparent point source. A second function of the mirror 104 is that of a scan angle amplifier (see for example, U.S. Pat. No. 7,959,290).

Line Scanning Ophthalmoscope

Figure 1B:
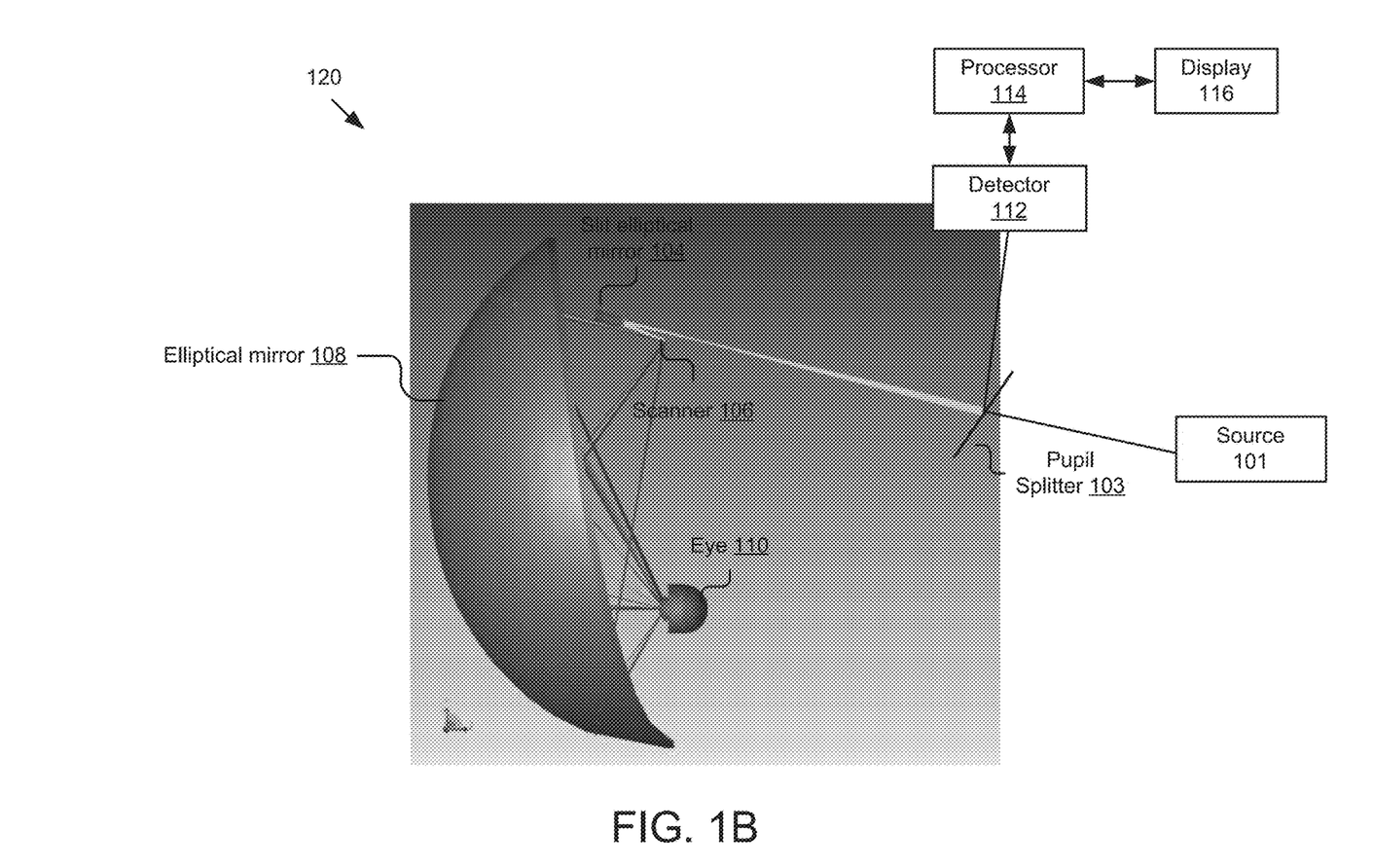
FIG. 1B illustrates a side view of a line scanning ophthalmoscope that is capable of performing a line scan of the retina.

FIG. 1B illustrates a side view of a general line scanning ophthalmoscope 120 that is capable of performing a line scan of the retina. Line scanning of the retina means scanning a line or a long slit over the retina and the image of the retina is reconstructed based on the scanned lines. In the line scan configuration, the arrangement of the elements 104, 106, and 108 remains the same as discussed above but now the first scanning element 102 is replaced with the pupil splitting element 103. So instead of requiring two scanning elements as in the case of point scanning of the retina, a pupil splitting element and a scanning element are used for the line scanning of the retina. The rotational axis of the scanning element 106 is substantially perpendicular to the line joining the two foci of the elliptical mirror 108 in slit elliptical mirror 104.

In the line scanning configuration, the pupil splitting element 103, the scanning element 106, and the pupil of the subject's eye 110 are optically conjugate to each other and serve as a pupil stop of the system. Through a lens, all light from the line/slit source (not shown) will pass through the pupil splitting element 103 and form a fan of light beams. The fan of light beams are reflected by the slit elliptical mirror 104 and conveyed to the scanning element 106, which is then conveyed to the elliptical mirror 108 and finally to the pupil of the subject's eye 110 to form an illuminated line/slit on the retina. The light which is scattered from the illuminated retina of the subject's eye 110 is conveyed back through the same optical path to the pupil splitting element 103, the detector 112, and the processor 114, which is used to produce a line/slit image of the subject's retina that can be displayed via the display 116. When the scanning element 106 scans, the illuminated line/slit on the retina of the subject's eye 110 will scan across the retina and a full ultra-wide field image of the retina can be reconstructed.

Similar to the functions of the slit elliptical mirror 104 discussed above with respect to the point scanning of the retina, in the line scanning embodiment, the mirror 104 serves as 1) the scan transfer function from the pupil splitting element 103 to the scanning element 106 and 2) the scan angle amplifier function.

Figure 1C:
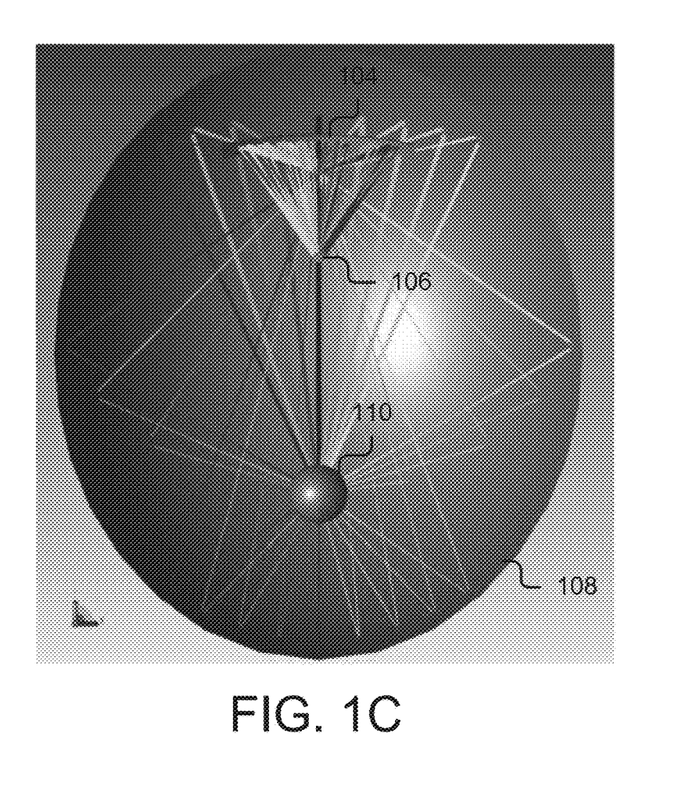
FIGS. 1C and 1D illustrate a front view and a 45 degree angle view of the point or line scanning ophthalmoscope, respectively.
Figure 1D:
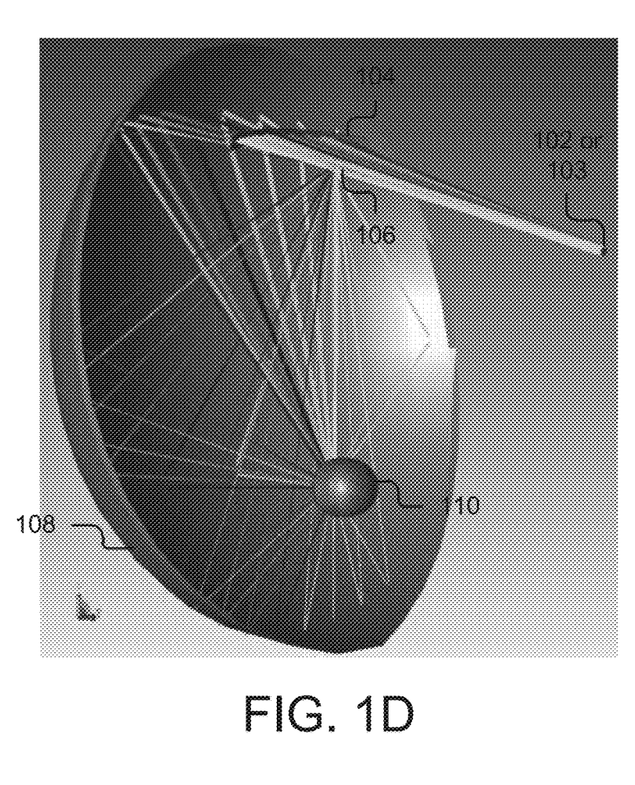

FIGS. 1C and 1D illustrate a front view and a 45 degree angle view of either the general point scanning ophthalmoscope 100 or line scanning ophthalmoscope 120, respectively.

Figure 3A:
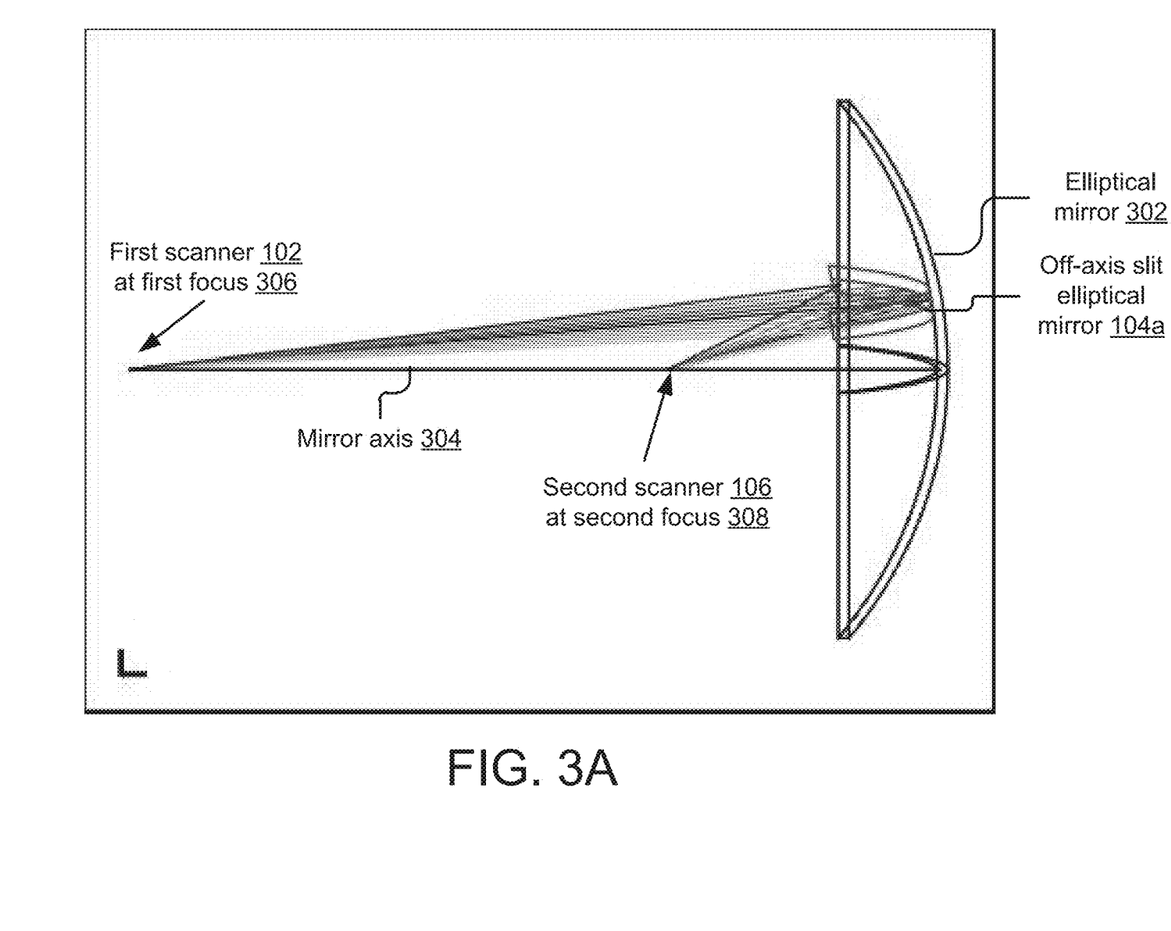
FIG. 3A illustrates an example off-axis arrangement of the slit.
Figure 3B:
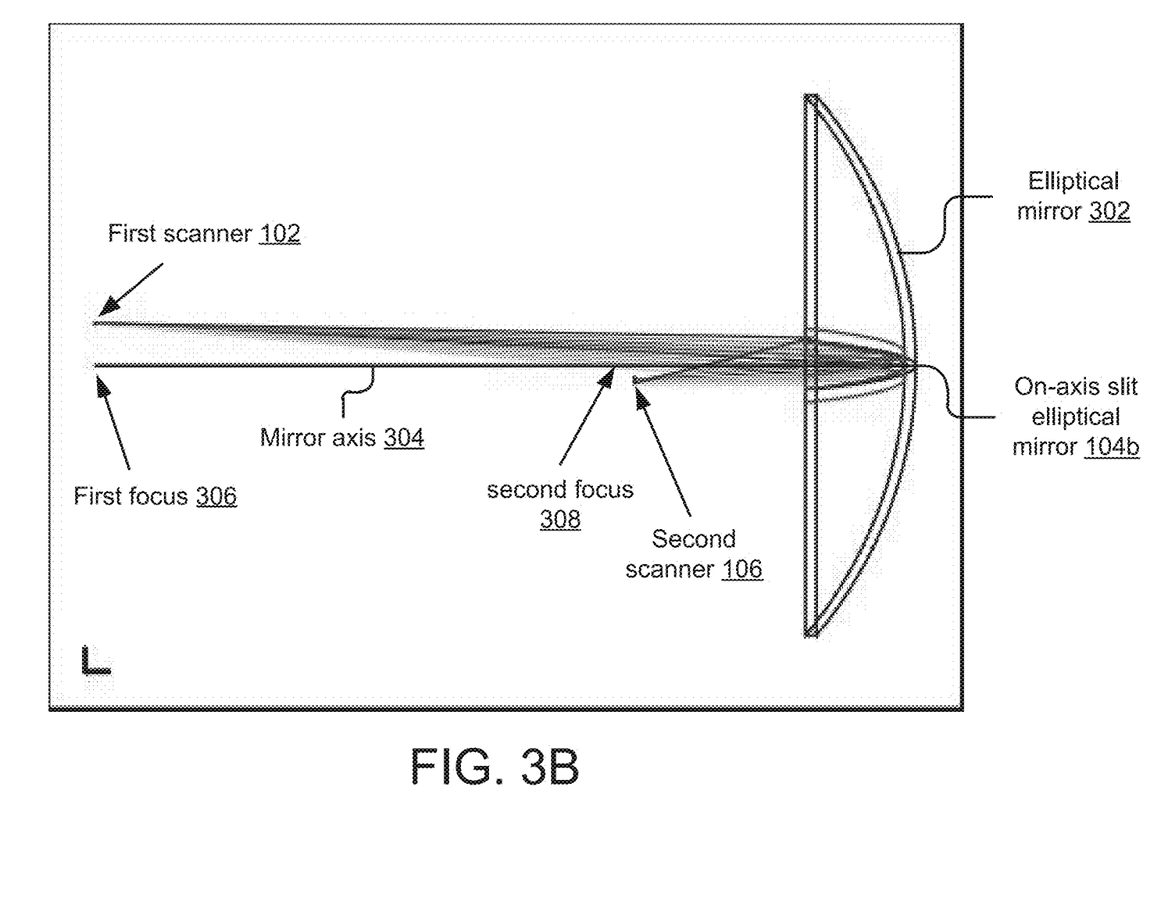
FIG. 3B illustrates an example on-axis arrangement of the slit.

FIGS. 3A and 3B illustrate two different arrangements of the slit elliptical mirror 104 that is discussed above with respect to FIGS. 1A-1D and FIGS. 2A and 2B. It should be recognized that FIGS. 3A and 3B as well as the other figures used to illustrate an implementation, an indication of a letter after a reference number or numeral, for example, "104a" is a specific reference to an element or component that is designated by that particular reference numeral. In the event a reference numeral appears in the text without a letter following it, for example, "104," it should be recognized that such is a general reference to different implementations of the element or component bearing that general reference numeral. By way of example, 104 is generally referring to the slit elliptical mirror shown in FIGS. 1A-1D and other figures while 104a or 104b in FIGS. 3A and 3B are referring to the two specific cases when the slit elliptical mirror 104 is positioned off-axis and on-axis, respectively.

In particular, FIG. 3A illustrates an off-axis arrangement of the slit elliptical mirror 104. Reference numeral 302 represents an example elliptical mirror and reference numerals 104a represents a slit of the elliptical mirror 302 which is located off-axis to the mirror axis 304. Reference numerals 306 and 308 indicate the two focus positions of the mirror 302. As depicted in FIG. 3A, when the slit is off-axis (indicated by reference numeral 104a), the two scanning elements 102 and 106 are located at the focus positions of the mirror 302. The components 104a, 102, and 106 are arranged such that when the light hits the off-axis slit 104a, the scanning element 106 doesn't block light from the first scanning element 102.

Referring now to FIG. 3B, when the slit is on-axis (indicated by reference numeral 104b), the two scanning elements 102 and 106 are offset from the two focus positions 306 and 308 but are located near to these positions. Here also the components 104b, 102, and 106 are arranged such that when the light hits the on-axis slit 104b, the scanning element 106 doesn't block light from the first scanning element 102.

Line Scanning Ophthalmoscope with Two Elliptical Mirrors

Figure 4A:
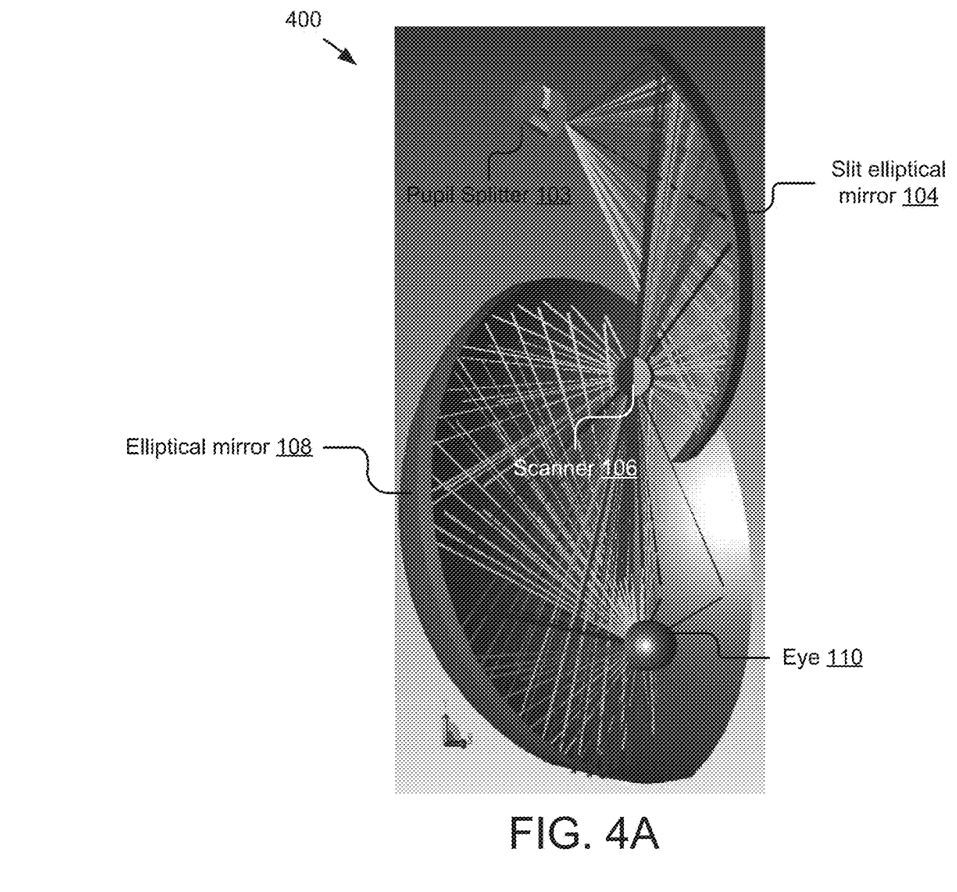
FIG. 4A illustrates a 45 degree angle view of an alternative line scan ophthalmoscope that is capable of performing line scanning of the retina of an eye using a slit and an elliptical mirror.

FIG. 4A illustrates a 45 degree angle view of an alternative line scan ophthalmoscope 400 that is capable of performing line scanning of the retina of an eye 110 using a slit and an elliptical mirror. As mentioned elsewhere herein, the slit could be a slit of an aspherical mirror and the instead of elliptical mirror it could be an aspherical mirror. The line scan ophthalmoscope 400 comprises a source of collimated/uncollimated light, such as the source 101 (not shown), a pupil splitting element 103, a slit elliptical mirror 104, a scanning element 106, and an elliptical mirror 108. Although not shown, it should be understood that the line scan ophthalmoscope 400 also includes the detector 112, the processor 114, and the display 116. Note that likewise numerals are used to refer to the same or similar elements/components, which were discussed above with respect to at least FIG. 1B. Also note that these elements/components perform the line scanning of the retina in the same way as discussed above with respect to at least FIG. 1B and hence, the description will not be repeated here.

Figure 4B:
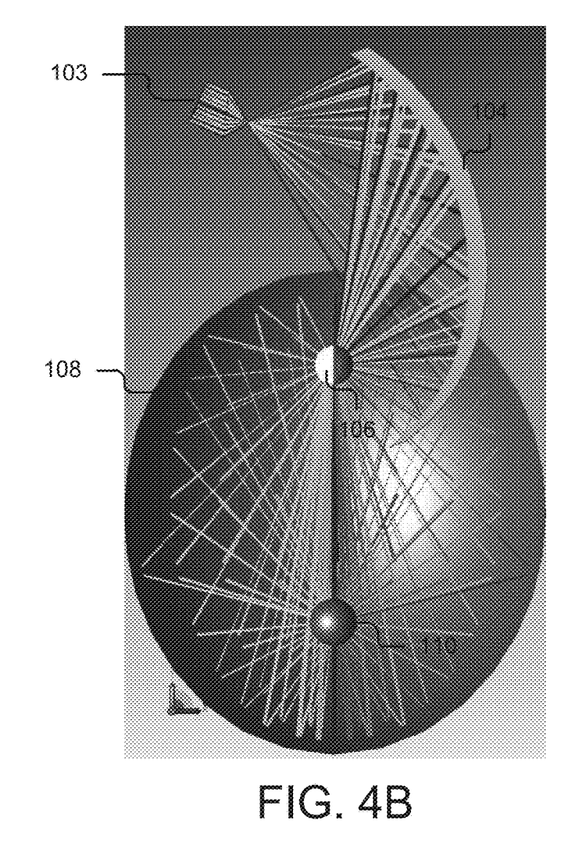
FIGS. 4B and 4C illustrate a front view and a side view of the line scan ophthalmoscope, respectively.
Figure 4C:
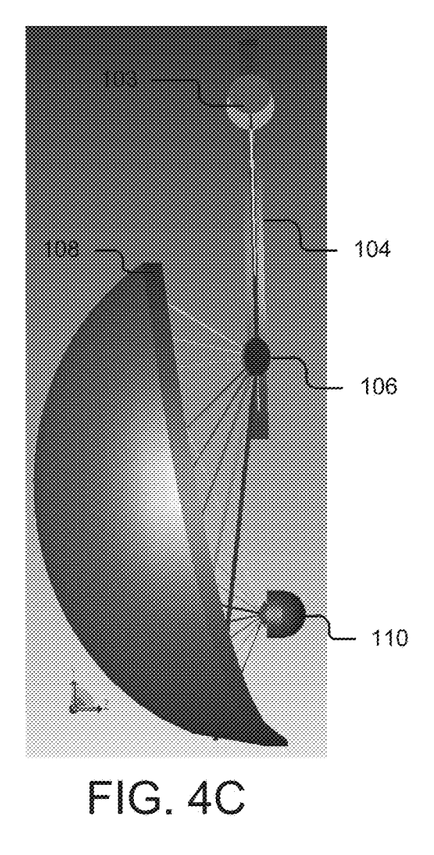

The line scan ophthalmoscope discussed herein with respect to FIGS. 4A-4C is different from the line scan ophthalmoscope discussed above with respect to FIG. 1B in the way that one or more of the components 103, 104, 106, and 108 are arranged. For instance, here the rotational axis of the scanning element 106 is substantially parallel to the line joining the two foci of the elliptical mirror 108. The advantage of such an arrangement depicted in FIGS. 4A-4C is that the angular distortion in the vertical direction can be cancelled out if the two elliptical mirrors 104 and 108 are designed properly.

FIGS. 4B and 4C illustrate alternate views of this line scan ophthalmoscope. In particular, FIG. 4B shows a front view and FIG. 4C shows a side view.

Point Scanning Ophthalmoscope with Two Elliptical Mirrors/One Elliptical Mirror

Figure 5A:
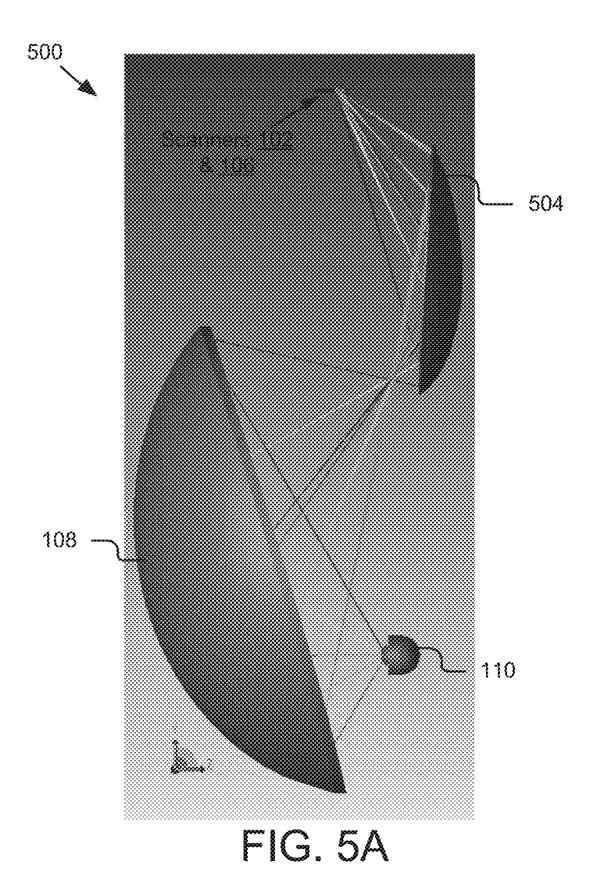
FIG. 5A illustrates a side view of a point scan ophthalmoscope that is capable of performing point scanning of the retina of an eye using two elliptical mirrors.
Figure 5B:
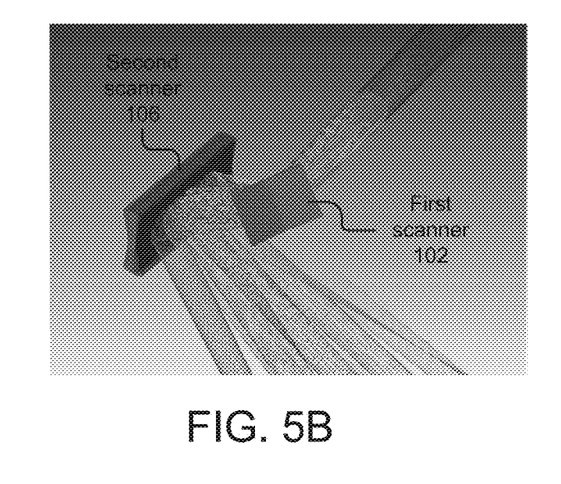
FIG. 5B shows arrangement of two scanners or scanning elements placed next to each other without optical relay between them.
Figure 5C:
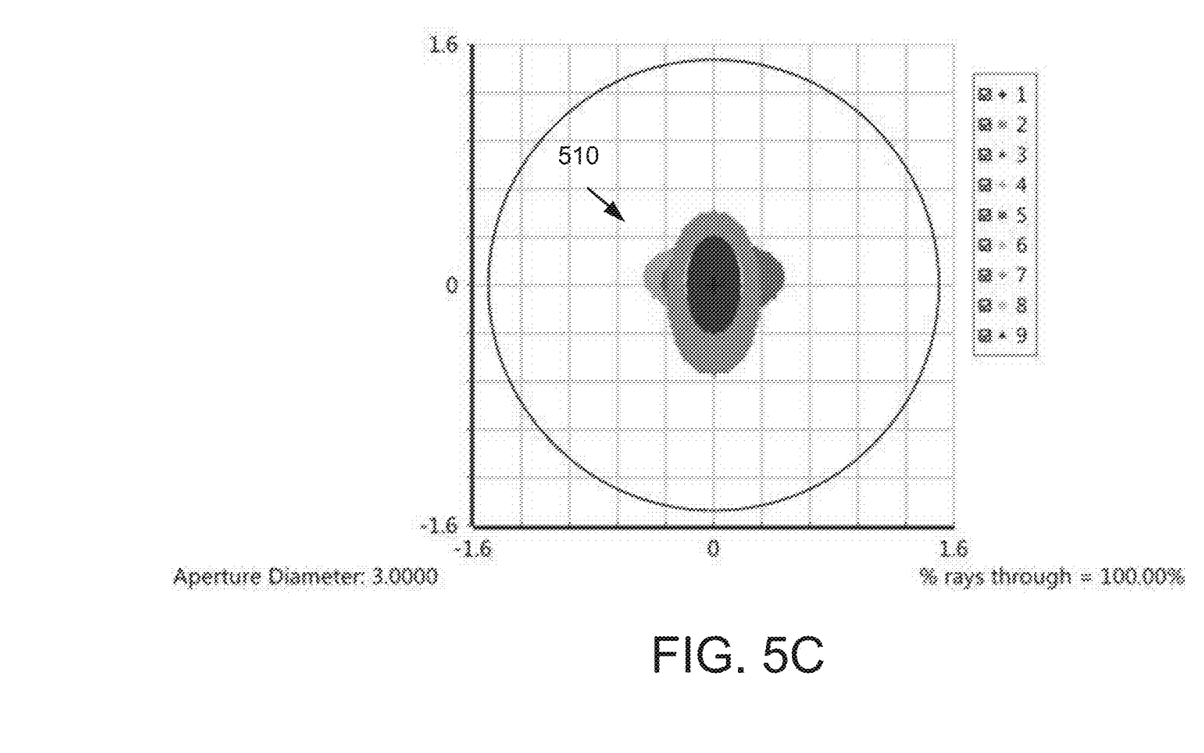
FIG. 5C illustrates footprint of scanning beam on the pupil based on such an arrangement of the two scanners or scanning elements.

FIG. 5A illustrates a side view of a point scan ophthalmoscope 500 that is capable of performing point scanning of the retina of an eye 110 using two elliptical mirrors. The point scan ophthalmoscope 500 comprises a source of collimated/uncollimated light, such as the source 101 (not shown), two scanning elements 102 and 106, a first elliptical mirror 504, and a second elliptical mirror 108. The two elliptical mirrors 504 and 108 are arranged such that they cancel out the angular distortion along the long axis of these mirrors. Although not shown, it should be understood that the point scan ophthalmoscope 500 also includes the detector 112, the processor 114, and the display 116. Note that likewise numerals are used to refer to the same or similar elements/components, which were discussed above with respect to at least FIG. 1A and FIGS. 4A-4C. Also note that these elements/components perform the point scanning of the retina in the same way as discussed above with respect to at least FIG. 1A and hence, the description will not be repeated here.

The point scan ophthalmoscope 500 discussed herein with respect to FIGS. 5A-5E is different from point line scan ophthalmoscope 100 discussed above with respect to FIG. 1A in the way that the two scanning elements 102 and 106 are arranged. For instance, the two scanning elements 102 and 106 are placed next to each other with a certain defined distance (see FIG. 5B) without optical relay between them (i.e., light transmission from one scanning element to another is direct and is not carried out by a mirror in between them). The advantage of placing the two scanning elements this way is that 1) no beam pre-positioning is necessary, 2) no optical relay is necessary, 3) without beam pre-positioning and optical relay, the system can be more compact and cost effective, and 4) one or two elliptical mirrors having astigmatism can be used to image the two scanning elements 102 and 106 to the same spot of the pupil of the subject's eye 110. This is further illustrated in FIG. 5C that shows an example footprint of the scanning beam on the pupil (indicated by reference numeral 510) formed based on such an arrangement of the two scanning elements.

Figure 5D:
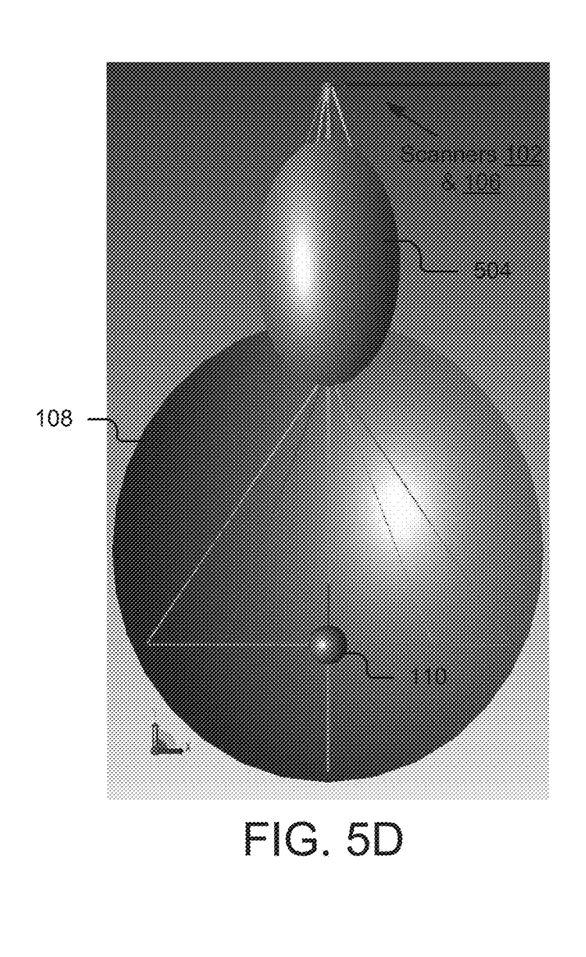
FIGS. 5D and 5E illustrate a front view and a 45 degree angle view of the point scan ophthalmoscope, respectively.
Figure 5E:
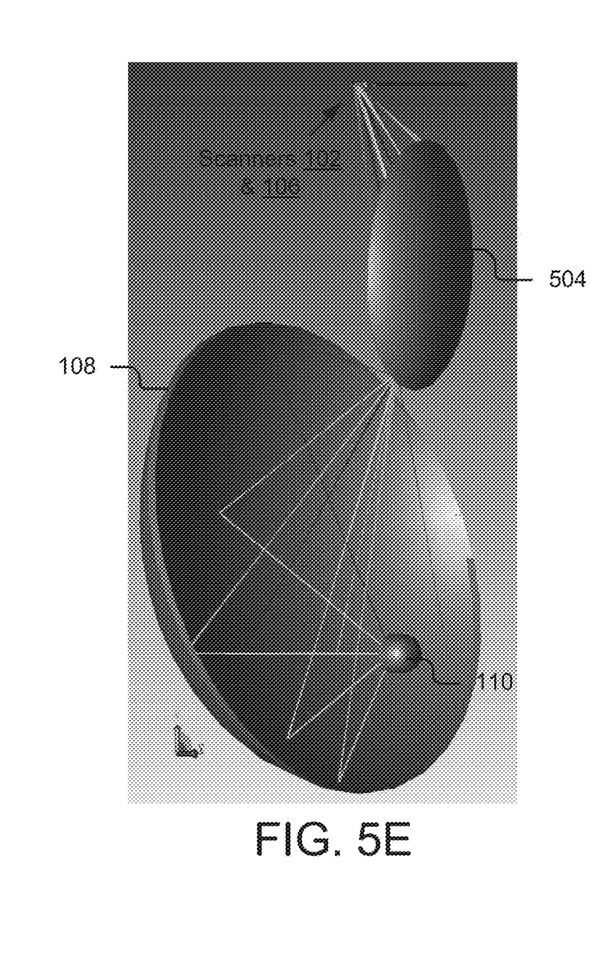

FIGS. 5D and 5E illustrate alternate views of this point scan ophthalmoscope. In particular, FIG. 5D shows a front view and FIG. 5E shows a 45 degree angle view.

Figure 6A:
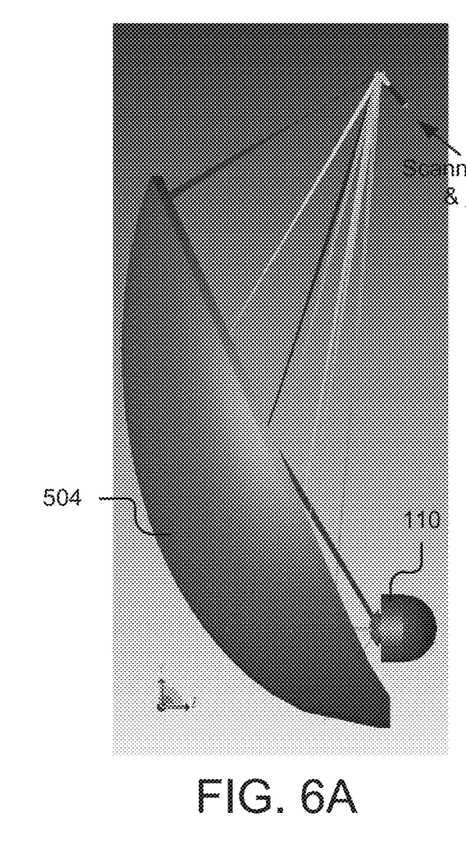
FIGS. 6A-6C illustrate a side view, a front view, and a 45 degree angle view, respectively, of an alternative point scan ophthalmoscope that is capable of performing point scanning of the retina of an eye using one elliptical mirror.
Figure 6B:
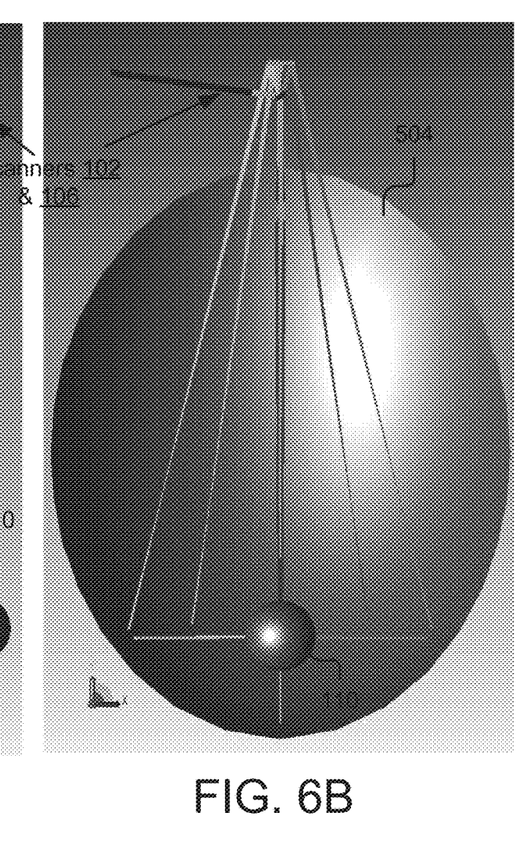
Figure 6C:
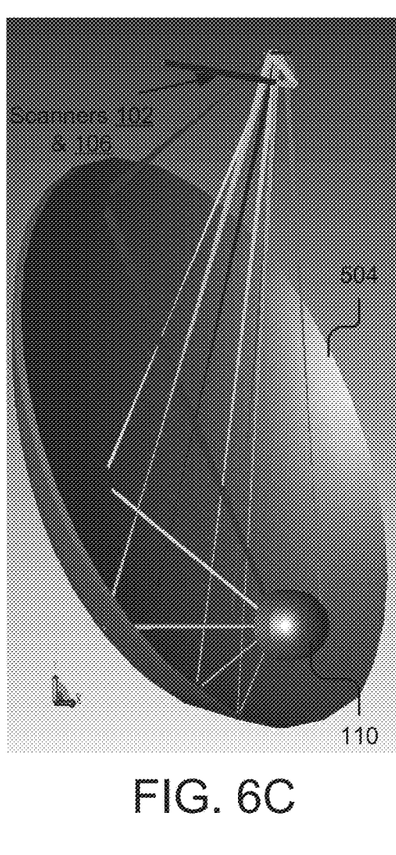

In some embodiments, the point scanning as discussed with respect to FIGS. 5A-5E is also possible with only one elliptical mirror. FIGS. 6A-6C illustrate a side view, a front view, and a 45 degree angle view, respectively, of a point scan ophthalmoscope that is capable of performing point scanning of the retina of an eye using one elliptical mirror 504. It should be understood that with only one elliptical mirror 504, there will be angular distortion along the long axis of the elliptical mirror 504.

As discussed elsewhere herein, the embodiments discussed with reference to FIGS. 5A-5E and 6A-6C can be generalized to function with aspherical mirrors and slits of aspherical mirrors and are within the scope of the present disclosure.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof.

The invention claimed is:

1. A scanning ophthalmoscope for scanning the retina of an eye through the pupil, said apparatus comprising:
   a light source for illuminating the retina with one or more rays of light;
   at least one aspherical mirror having astigmatism;
   a first scanning element; and
   a second scanning element, wherein the first scanning element and the second scanning element are placed in a way such that (a) a ray of light from the light source when incident on the first scanning element travels to the second scanning element without being reflected by the aspherical mirror, and (b) the pupil is imaged by the at least one aspherical mirror having astigmatism to the first scanning element for rays travelling in a first plane, and the pupil is imaged by either the at least one aspherical mirror or a second aspherical mirror having astigmatism to the second scanning element for light rays travelling in the plane perpendicular to the first plane.

2. The scanning ophthalmoscope as recited in claim 1, wherein the aspherical mirror is an elliptical mirror.

3. The scanning ophthalmoscope as recited in claim 2, wherein said ophthalmoscope includes two aspherical mirrors.

4. The scanning ophthalmoscope as recited in claim 2, wherein said light source is a source of collimated light.

5. The scanning ophthalmoscope as recited in claim 2, wherein said light source is a source of uncollimated light.

* * * * *

UNITED STATES PATENT AND TRADEMARK OFFICE
CERTIFICATE OF CORRECTION

PATENT NO.        : 10,201,275 B1
APPLICATION NO.   : 15/415116
DATED             : February 12, 2019
INVENTOR(S)       : Yue Qiu et al.

Page 1 of 1

It is certified that error appears in the above-identified patent and that said Letters Patent is hereby corrected as shown below:

In the Specification

In Column 5, Line 56, delete "1A-ID" and insert -- 1A-1D --, therefor.

Signed and Sealed this
Thirtieth Day of July, 2019

Andrei Iancu
*Director of the United States Patent and Trademark Office*